US00PP29094P3

(12) United States Plant Patent
Sidhu

(10) Patent No.: US PP29,094 P3
(45) Date of Patent: Mar. 13, 2018

(54) ***GAULTHERIA* PLANT NAMED 'GAULSIDH11'**

(50) Latin Name: *Gaultheria procumbens*
Varietal Denomination: Gaulsidh11

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 15/330,620

(22) Filed: Oct. 19, 2016

(65) Prior Publication Data

US 2017/0142884 P1 May 18, 2017

(30) Foreign Application Priority Data

Nov. 17, 2015 (CA) ..... PBR 15-8748

(51) Int. Cl.
*A01H 5/08* (2006.01)

(52) U.S. Cl.
USPC ..... Plt./226

(58) Field of Classification Search
USPC ..... Plt./226
CPC ..... A01H 5/08; A01H 5/02; A01H 5/00
See application file for complete search history.

*Primary Examiner* — June Hwu
(74) *Attorney, Agent, or Firm* — Penny J. Aguirre

(57) ABSTRACT

A new cultivar of *Gaultheria* plant named 'Gaulsidh11' that is characterized by its vigorous growth habit, its leaves that are elongated in shape, its good berry set with good distribution along the stem, its young foliage that is glossy, and its berries that are medium in size.

2 Drawing Sheets

Botanical classification: *Gaultheria procumbens*.
Cultivar designation: 'Gaulsidh11'.

CROSS REFERENCE TO RELATED APPLICATIONS

This application is co-pending with U.S. Plant Patent Applications filed for plants derived from the same breeding program that are entitled *Gaultheria* Plant Named 'Gaulsidh5' (U.S. Plant patent application Ser. No. 15/330,619).

BACKGROUND OF THE INVENTION

The present invention relates to a new and distinct cultivar of *Gaultheria procumbens*, known as *Gaultheria* 'Gaulsidh11'. 'Gaulsidh11' and is hereinafter referred to by its cultivar name 'Gaulsidh11'.

'Gaulsidh11' originated from the open pollination of unnamed and unpatented seedlings of *Gaultheria procumbens* in the Inventor's greenhouse production bed in Mission, B.C., Canada. The exact parentage is therefore unknown. 'Gaulsidh11' was selected as a single unique plant in 2011 from amongst the resulting seedlings.

Asexual reproduction of the new cultivar was first accomplished by tissue culture using meristemac tissue under the direction of the Inventor in Mission, B.C., Canada in April of 2011. Asexual propagation of the new cultivar by tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Gaulsidh11' as a new and unique cultivar of *Gaultheria*.

1. 'Gaulsidh11' exhibits a vigorous growth habit.
2. 'Gaulsidh11' exhibits leaves that are elongated in shape.
3. 'Gaulsidh11' exhibits high berry set.
4. 'Gaulsidh11' exhibits young foliage that is glossy.
5. 'Gaulsidh11' exhibits berries that are medium in size.

Typical plants of the parent species of 'Gaulsidh5', *Gaultheria procumbens*, are similar to 'Gaulsidh5' in berry size. Typical plants of *Gaultheria procumbens* differ from 'Gaulsidh11' in having a less vigorous growth habit, less berry set and weaker distribution of berries along the stem and leaves that are less elongated. 'Gaulsidh11' can be most closely compared to *Gaultheria procumbens* 'Gaulsidh5'. 'Gaulsidh5' differs from 'Gaulsidh11' in having berries that are larger in size with less fruit set, leaves that are less elongated in shape and a less vigorous growth habit.

BRIEF DESCRIPTION OF THE DRAWINGS

The accompanying colored photographs illustrate the overall appearance and distinct characteristics of the new *Gaultheria*. The photographs were taken of a plant about 6-months in age as grown outdoors in a 4-inch containers in Elma, Wash.

The photograph in FIG. 1 provides a top view and a side view of the plant habit of 'Gaulsidh11'.

Figure 1:
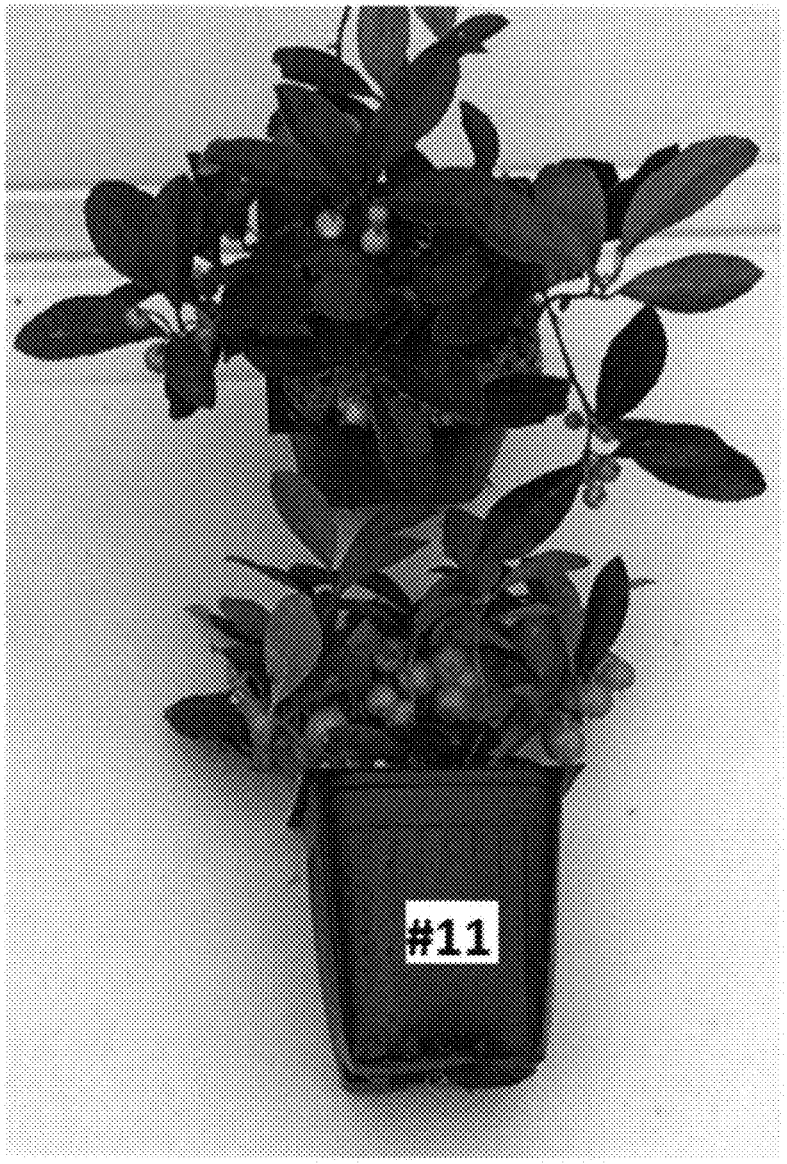
Figure 2:
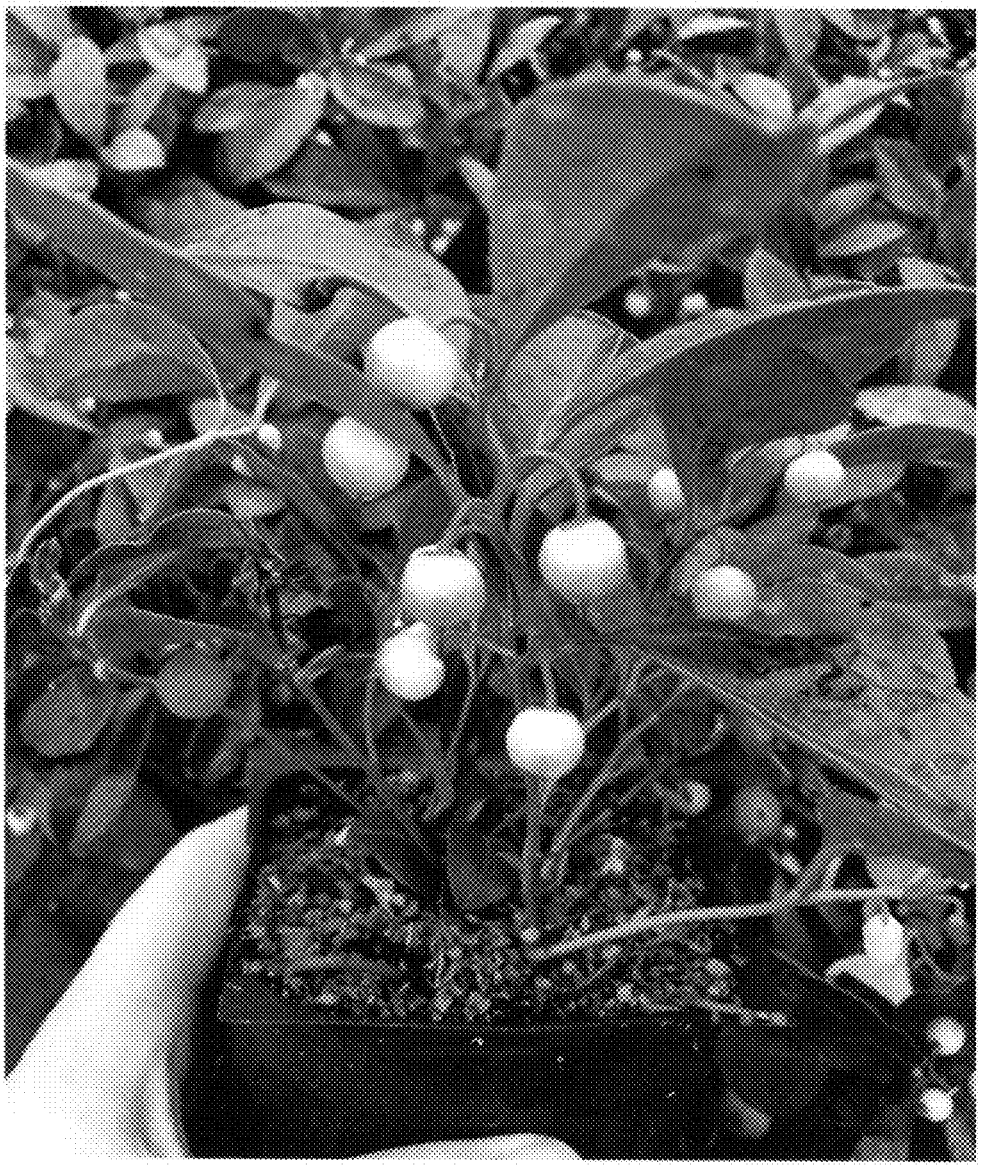

The photograph in FIG. 2 provides a close-up view of maturing and mature fruit of 'Gaulsidh11'.

The colors in the photographs may differ slightly from the color values cited in the detailed botanical description, which accurately describe the colors of the new *Gaultheria*.

DETAILED BOTANICAL DESCRIPTION OF THE PLANT

The following is a detailed description of six month-old plants of the new cultivar grown outdoors in 4-inch containers in Elma, Wash. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Late spring to late summer.

*Plant type.*—Evergreen shrub.

*Plant habit.*—Broadly spreading, groundcover once established.

*Height and spread.*—11 cm in height and 11 cm in width as grown in a 4-inch container.

*Cold hardiness.*—At least in U.S.D.A. Zones 3 to 8.

*Diseases and pests.*—No resistance or susceptibility to diseases or pests has been observed.

*Propagation.*—Tissue culture (preferred).

*Root development.*—An average of 4 months to fully root in a 4-inch container from a plug produced by tissue culture and an average of 4 months to fully root in a one-gallon container from a 4-inch container.

*Growth rate and vigor.*—Vigorous.

Stem description:

*Shape.*—Round.

*Stem color.*—New and mature growth; a blend of 144A and 144B and 184A.

*Stem size.*—Up to 9 cm in length and 1 mm in width.

*Stem surface.*—Moderately glossy.

*Stem strength.*—Strong.

*Branching.*—Freely branched, an average of 11 basal branches.

*Branch angle.*—Upright to outward.

*Branch internode length.*—Up to 5.5 cm.

Foliage description:

*Leaf shape.*—Ovate.

*Leaf division.*—Simple.

*Leaf base.*—Acute.

*Leaf apex.*—Acute.

*Leaf fragrance.*—Wintergreen if crushed.

*Leaf venation.*—Pinnate, upper surface matches leaf color; main vein a blend of N144A and 182A, lower surface color; a blend of 184A and 184C.

*Leaf margins.*—Irregularly serrate.

*Leaf arrangement.*—Alternate and clustered near tips.

*Leaf attachment.*—Petiolate.

*Leaf number.*—Average of 4 per branch.

*Leaf surface.*—Upper and lower surface young foliage; glabrous, glossy and leathery, Upper and lower surface mature foliage; glabrous, satiny, and leathery.

*Leaf size.*—Average of 5.5 cm in length 2.5 cm in width.

*Leaf color.*—Emerging leaves upper and lower surface; 175B, young leaves upper surface; a blend of 143A suffused with 185A, mature leaves upper surface; a blend of 139A and 141A and suffused with 185A, young and mature lower surface; 147C suffused with 181C.

*Petioles.*—Average of 5 mm in length and 2 mm in width, upper and lower surfaces are dull, color; upper and lower surfaces 184A.

*Stipules.*—Average of 2 to 4 per 6 cm branch, 1 mm in length and width, matches stem color, both surfaces glabrous and glossy.

Inflorescence description:

*Inflorescence.*—Axillary and terminal clusters of individual flowers.

*Inflorescence size.*—Average of 2.5 cm in length and width.

*Lastingness of inflorescence.*—Average of 2 weeks, self cleaning (sepals and petals).

*Number of flowers.*—3 to 5 per panicle, average of 35 per plant.

*Flower fragrance.*—None.

*Flower buds.*—Ovate in shape, average of 7 mm in length and 4.5 mm in width, a blend of 156D and 156A in color, satiny surface.

*Flower size.*—Average of 8 mm in length and 6 mm in width.

*Corolla.*—Urceolate in shape, comprised of 5 fused ovate shaped petals with rounded tips (5%) free that are curled under, free curled parts are 1 mm in length and width, color a blend of 156D and 156A on both surfaces when opening and mature, both surfaces are satiny, glabrous, slightly translucent, and very slightly ribbed.

*Calyx.*—Rotate and starred in arrangement, average of 2.5 mm in length and 6 mm in diameter.

*Sepals.*—5, average of 2.5 mm in length and 2 mm width, color is a blend of 150C, 150A and 155B, glabrous on both surfaces, apex acute with small apiculate tip.

*Bracts.*—2 small bracts, an average of 1 mm in length and width, ovate in shape, truncate base, acute apex, glossy on both surfaces, and 146A in color.

*Peduncles.*—Round, held at a downward angle to stem, at a an average of 6 cm in length and 1 mm in width, young peduncle color; 144A in color, mature peduncle color; 183A, pubescent surface.

*Pedicels.*—None.

Reproductive organs:

*Androecium.*—Average of 10 stamens, anthers are dorsifixed, narrow deltoid in shape, 164A in color and 2 mm in length, filaments oblong in shape are 4 mm in length, 1 mm in width and NN155C in color, highly pubescent, pollen is moderate in quantity and NN155C in color.

*Gynoecium.*—1 pistil, stigma is club-shaped, 1 mm in length and width, and 145D in color, style is an average of 6 mm in length and 157D in color, ovary is round in shape, 6-parted, 2.5 mm in diameter and depth, and 145D in color.

Fruit description:

*Type.*—Berry.

*Number.*—8 to 10 per lateral branch (high fruit set) with good distribution along the stem.

*Fruit size.*—Average of 1.5 cm and 1.2 cm in width.

*Fruit skin color.*—Young fruit; a blend of 155A, 69D and 62A, mature fruit; closest to 62A and slightly more red.

*Fruit flesh.*—NN155D in color, glistening and spongy in texture.

*Fruit surface.*—Glossy and glabrous.

*Fruit shape.*—Rounded with indented apex and 5 bluntly acute extended tips, tip size is 5 mm in length and 6 mm in width.

*Seeds.*—Few cylindrical shaped seeds, glossy surface, less than 1 mm in length and width, 162A in color.

It is claimed:

1. A new and distinct cultivar of *Gaultheria* plant named 'Gaulsidh11' as herein illustrated and described.

* * * * *